United States Patent [19]

Zubrzycki

[11] 4,446,230

[45] May 1, 1984

[54] **TEST METHOD FOR THE LABORATORY DIAGNOSIS OF GONORRHEA AND TEST STRAIN OF *NEISSERIA GONORRHOEAE***

[75] Inventor: Leonard J. Zubrzycki, Pennsauken, N.J.

[73] Assignee: Temple University of the Commonwealth System of Higher Education, Philadelphia, Pa.

[21] Appl. No.: 317,023

[22] Filed: Oct. 30, 1981

[51] Int. Cl.$^3$ .................. C12Q 1/68; C12Q 1/04; C12Q 1/12; C12N 1/20

[52] U.S. Cl. .................................... 435/6; 435/34; 435/37; 435/253; 435/871

[58] Field of Search .................. 435/34, 37, 6, 871, 435/253

[56] References Cited

U.S. PATENT DOCUMENTS 3,930,956  1/1976  Juni .................................. 195/103.5

OTHER PUBLICATIONS

John J. Wendall et al., The Journal of Infectious Diseases, vol. 142, No. 5, p. 775; 1980.
European Search Report.
Sexually Transmitted Diseases, vol. 7, Oct./Dec. 1980, American Veneral Disease Association (U.S.)-L. Zubrzycki et al.
Abstracts of the Annual Meeting, 1975, American Society for Microbiology, P. Warner et al.
Chemical Abstracts, vol. 65, 1966, col. 20544b, Columbus, Ohio (U.S.), P. F. Sparling.
Difco Manual of Dehydrated Culture Media and Reagents for Microbiological and Clinical Laboratory Procedures, 9th Ed. Difco Laboratories, pp. 116–121.
Difco Technical Information, Dec. 1976, Difco Laboratories, Technical Information No. 0580, Detroit, Mich.
Kellog, Jr., et al., Laboratory Diagnosis of Gonorrhea, Cumitech., Amer. Soc. Microbiol., 1976.
Transgrow, a Medium for Transport and Growth of *Neisseria gonorrhoeae* and *Neiseria meningitidis,* Martin, Lester, HSHMA.
Health Rep. 86:30, 1971.
Schmaly, Martin, Domescik, J. Am. Med. Assoc. 210:312, 1969.
Sensitivity and Reproducibility of Thayer-Martin Culture Medium in Diagnosing Gonorrhea in Women, Caldwell, Price, Pazin, Cornelius, Am. J. Obstr. Gynecol. 109:463, 1971.
Clin. Microbiol. 4:71.
Bawdon, Juni, Britt, J. Clin. Microbiol. 5:108, 1977.
Sarafian, Yound, J. Med. Microbiol. 13:291, 1980.
Crawford, Sex. Trans. Dis. 5:165, 1978.
Kellogg, Peacock, Deacon, Brown, Pirkle, J. Bacteriol. 85:1274, 1963.
Wharton, Zubrzycki, J. Bacteriol. 127:1579, 1976.
Maier, Zubrzycki, Coyle, Antimocrob. Ag. Chemo. 7:676, 1975.
Lennette, Spaulding, Truant, Manual of Clinical Microbiol., Amer. Soc. Microbiol., pp. 423, 933, 1974.

*Primary Examiner*—Robert J. Warden
*Attorney, Agent, or Firm*—Paul & Paul

[57] ABSTRACT

A strain of *Neisseria gonorrhoeae* ATCC 31953 is described which is abnormal in that it has characteristically poor growth on chocolate agar at a temperature range of about 30° C. to about 37° C. in a $CO_2$ atmosphere suitable for growth of *N. gonorrhoeae*. This strain is resistant to nalidixic acid at the 5–10 mcg/ml level and resistant to streptomycin at the 1000 mcg/ml level or greater. *N. gonorrhoeae* ATCC 31953 is a test strain suitable for use in the method described for the laboratory diagnosis of gonorrhea. The method comprises the steps of (1) applying a non-toxic preparation of a patient's specimen material, directly to a culture of *Neisseria gonorrhoeae* ATCC 31953, which has abnormal growth characteristics, which is in or on a biological medium suitable for growth of normal *Neisseria gonorrhoeae,* and observing for the restoration of normal growth to the abnormal growth strain *Neisseria gonorrhorae* ATCC 31953, in or on the biological medium of step (1), under conditions normal for growth of *Neisseria gonorrhoeae*. The observence of growth indicates positive detection of *N. gonorrhoeae* DNA.

16 Claims, No Drawings

TEST METHOD FOR THE LABORATORY DIAGNOSIS OF GONORRHEA AND TEST STRAIN OF *NEISSERIA GONORRHOEAE*

BRIEF SUMMARY OF THE INVENTION

The standard laboratory diagnosis of gonorrhea depends on isolation and subsequent identification of *Neisseria gonorrhoeae* by colony morphology, microscopic examination, biochemical or serologic tests (Kellog, Jr., et al., Laboratory Diagnosis of Gonorrhea, Cumitech, Amer. Soc. Microbiol., 1976). Although gram stain examination can be used to diagnose gonococcal urethritis, this technique lacks sensitivity in detecting infections of the cervix, rectum or oropharynx. Other diagnostic methods, such as serologic testing or direct fluorescent antibody staining, have not proven useful.

Because *N. gonorrhoeae* loses viability rather quickly, the best procedure for isolating gonococci is to culture a specimen as soon as possible. This requires special facilities since it is necessary to incubate the inoculated culture media at 35° C.–37° C. in a $CO_2$ atmosphere. When proper facilities are not available, specimens can be sent to a laboratory in Amies' or Stuart's transport medium or in a transport and growth medium such as Transgrow (Martin, Lester, HSMHA Health rep. 86:30, 1971). The latter procedures are not nearly as good as immediate culturing which itself is about 90–95% sensitive in detecting gonococci (Schmaly, Martin, Domescik, J. Am. Med. Assoc. 210:312, 1969; Caldwell, Price, Pazin, Cornelius, Am. J. Obstr. Gynecol. 109:463, 1971).

In 1976, a transformation test was reported which could be used to identify a clinical isolate as *N. gonorrhoeae* and thereby to help diagnose gonorrhea (Janik, Juni, Heym, J. Clin. Microbiol. 4:71; Juni U.S. Pat. No. 3,930,956). A transformation test depends on detecting gonococcal DNA as compared to a culture technique which depends on isolating colonies. In preliminary laboratory studies, the test appeared to be a useable alternative to standard porcedures for identifying colonies of *N. gonorrhoeae* (Bawdon, Juni, Britt, J. Clin. Microbiol. 5:108, 1977; Sarafian, Young, J. Med. Microbiol. 13:291, 1980). However, in a field trial, done in collaboration with the Centers for Disease Control, using specimens obtained from clinic patients, the test described was found to be insensitive and nonspecific for the laboratory diagnosis of gonorrhea infections.

The Juni transformation test depends on DNA from gonococci in a colony or a specimen, to contain genes which can correct a nutritional deficiency of a test strain of *N. gonorrhoeae*, i.e. the test strain cannot grow on a special test medium unless it is given a particular nutrient. However, this strain can take up and incorporate gonococcal DNA (genes) into its genome, so that it is transformed with such genes and can now grow on the special test medium. If the gonococci of a colony, or in a specimen, and the test strain happened to have the same nutritional deficiency, then the test strain cannot be transformed to grow on the special test medium, thereby preventing detection of *N. gonorrhoeae* DNA from a colony or specimen. Since it is known that there is a variety of nutritional variants of *N. gonorrhoeae* which infect humans (Crawford, Sex. Trans. Dis. 5:165, 1978), the Juni test obviously requires a battery of test strains with different nutritional deficiencies in order to cover the spectrum of possibilities in any one test situation.

The Juni test requires the use of two culture media, one of which is so specialized that it is not available in a routine diagnostic laboratory. The technique for extracting DNA calls for using surfactants such as sodium dodecyl sulfate at a concentration which is at the borderline level of toxicity for the test strains. This could negate potentially positive results. The transformation technique involves a preliminary incubation period of the DNA and the test strain, followed by a second step which involves subculturing the DNA-test strain mixture onto the specialized medium. After 24 hours of incubation the results of their test are barely visible to the naked eye. One needs a microscope to detect the growth of colonies which indicates a positive result (Bawdon et al, J. Clin. Microbiol. 5:108, 1977).

I have now discovered that a novel test strain of *N. gonorrhoeae* ATCC 31953, when utilized in accordance with the novel method of this invention, enables an accurate laboratory diagnosis of gonorrhea to be made by detecting *N. gonorrhoeae* DNA. The test strain, *N. gonorrhoeae* ATCC 31953, has been deposited with the American Type Culture Collection, Rockville, MD. During the term of this patent it may be obtained from the depository by anyone. This novel test strain is abnormal in that it barely grows in conditions considered to be optimum for normal *N. gonorrhoeae* and has certain antibiotic resistance genes introduced by genetic recombination.

The method of this invention comprises the steps of (1) applying a non-toxic preparation of a patient's specimen material, directly to a culture of *Neisseria gonorrhoeae* ATCC 31953 which has abnormal growth characteristics, which is in or on a biological medium suitable for growth of normal *Neisseria gonorrhoeae*, and (2) observing for the restoration of normal growth to the abnormal growth strain *Neisseria gonorrhoeae* ATCC 31953, in or on the biological medium of step (1) under conditions normal for growth of *Neisseria gonorrhoeae*. The observance of growth indicates positive detection of *N. gonorrhoeae* DNA.

In accordance with this invention a test kit is provided which enables the method of this invention to be performed, which kit includes a test strain of *N. gonorrhoeae* which grows poorly at about 36° C. on or in a biological medium, and may optionally contain other components required to perform the test such as a biological medium capable of supporting growth of a test strain, a base, an acid, a pH indicator, and necessary laboratory equipment and supplies.

The novel method of this invention requires only one test strain. It depends on a genetic characteristic common to all *N. gonorrhoeae* causing human infections, namely, the ability to grow at about 36° C. The invention permits the use of such biological media as common chocolate agar. Extracting gonococcal DNA from a patient's specimen material by the use of base and adjusting the pH of the preparation to a pH tolerated by *N. gonorrhoeae* ATCC 31953 with an acid results in a salt which is not toxic to the test strain. The procedures are very simple. Positive results are seen in 27–40 hours without the use of a microscope. In a field trial conducted in collaboration with the Centers for Disease Control, the new invention was found to be as sensitive and specific as the culture technique for the diagnosis of gonorrhea.

DETAILED DESCRIPTION OF THE INVENTION

I. Neisseria gonorrhoeae ATCC 31953

*Neisseria gonorrhoeae* ATCC 31953 is the test strain for use in the method of this invention, *N. gonorrhoeae* ATCC 31953, is abnormal in that it grows poorly on chocolate agar within a temperature range of from about 30° C. to about 37° C., in a $CO_2$ atmosphere. Specifically, this strain barely grows in conditions considered to be optimum for *N. gonorrhoeae* i.e., on common chocolate agar, at a temperature around 36° C. in a $CO_2$ atmosphere.

This strain is also resistant to nalidixic acid at the 5-10 mcg/ml level and resistant to streptomycin at the 1000 mcg/ml level or greater. Details of the mutation and the genetic recombination procedures which resulted in the isolation of *N. gonorrhoeae* ATCC 31953 follow.

The chemical mutagen, N-methyl-N'-nitro-N-nitrosoguanidine, was added at a final concentration of 25 mcg/ml to GC buffer (an aqueous solution of 1.5% peptone, such as Proteose Peptone, Difco, Detroit, Mich., 0.028 M potassium phosphate, dibasic and 0.007 M potassium phosphate, monobasic) which contained about $10^9$ cells of a common laboratory strain of *N. gonorrhoeae* prepared from colony types 1 or 2 (Kellogg, Peacock, Deacon, Brown, Pirkle, J. Bacteriol. 85:1274, 1963). After a 30 minute incubation of the mutagen-cell suspension in a water bath set for 37° C., the suspension was centrifuged to pellet the cells. The supernate was removed to discard the mutagen. The pelleted cells were resuspended in GC buffer. After centrifugation a second time, the pellet was again resuspended in GC buffer. The suspension was then plated on GC agar (in petri plates), which is GC medium base (GC buffer, 0.5% NaCl, 0.1% cornstarch, 1.0% agar) supplemented at a final concentration in gms/100 ml, with glucose 0.4 g, glutamine 0.01 g, cocarboxylase 0.00002 g, $Fe(NO_3)_3 \cdot 9H_2O$ 0.0005 g. The petri plates were incubated overnight at 30° C. and then switched to 37° C. for the second night of incubation. Small colonies were picked and tested for the inability to grow luxuriously at 37° C. on GC agar. A poor growing variant of *N. gonorrhoeae* judged to be potentially useful in the method of the invention was isolated in this manner and used to obtain the test strain having specific antibiotic resistance. The antibiotic resistance genes were introduced into this variant in the following manner.

DNA was extracted from the RW-2 strain of *N. gonorrhoeae* which contains the Nal gene conferring resistance to nalidixic acid at the 5-10 mcg/ml level (Wharton, Zubrzycki, J. Bacteriol. 127:1579, 1976). The DNA extraction procedure was accomplished by adding NaOH at a final concentration of 0.1 N to a suspension of RW-2 (containing approximately $1 \times 10^8$ cells/ml) in GC buffer. The extract was then neutralized with HCl.

Two-tenths ml of this neutralized extract containing RW-2 DNA was added to a 1.8 ml suspension of the variant (about $1 \times 10^8$ cells/ml) in GC buffer which contained approximately $10^{-3}$ M $CaCl_2$. After incubating the DNA-cell mixture for 30 min. in a water bath set for 30° C., 0.1 ml aliquots of the mixture were put onto, and then evenly spread on the surface of six petri dishes containing GC agar. After incubating the plates in a candle extinction jar for 4 hours, the GC agar was lifted from the petri dish and placed on top of another layer of GC agar which contained 10 mcg/ml Nal. This double-layered agar, with the DNA-cell mixture on the top, was incubated for about 40 hours at 30° C. in a $CO_2$ atmosphere. Of the many colonies which appeared, presumably resistant to Nal, twenty were selected at random and subcultured. Of these, one was selected as being best suited, at this time, for use in the method of this invention.

Using essentially the same procedures as just described, DNA from *N. gonorrhoeae* strain 24392 (Maier, Zubrzycki, Coyle, Antimocrob. Ag. Chemo. 7:676, 1975) was used to introduce the Str gene into the Nal variant. Of 14 isolates which were resistant to both antibiotics, Nal at the 5-10 mcg/ml level and Str at the 1000 mcg/ml level or greater, one was selected as being best suited as the test strain for use in the method of this invention, *N. gonorrhoeae* ATCC 31953. The test strain *N. gonorrhoeae* ATCC 31953 has morphological and biochemical characteristics generally like those of *Neisseria gonorrhoeae*.

II. Growth and Preparation of *Neisseria gonorrhoeae* ATCC 31953

*N. gonorrhoeae* ATCC 31953 is prepared for use in accordance with the method of this invention by growing it on the surface of GC agar at 30° C. in a $CO_2$ atmosphere suitable for *N. gonorrhoeae*, for example: a candle extinction jar; a $CO_2$ incubator; a $CO_2$ generating system such as Gas-Pak system (Baltimore, Biological Laboratories, Cockeysville, Md.). After overnight incubation, areas of colony growth on the agar plates having mostly colony types 1 and/or 2 (Kellogg, Peacock, Deacon, Brown, Pirkle, J. Bacteriol. 85:1274, 1963) are harvested with sterile cotton swabs which are inserted into 10-20 ml volumes of GC buffer containing 10-20% glycerol, in order to make a suspension equivalent to a number 4 or 5 McFarland standard (Lennette, Spaulding, Truant, Manual of Clinical Microbiol., Amer. Soc. Microbiol., p. 933, 1974). Selection of colony types 1 or 2 is required to ensure that *N. gonorrhoeae* ATCC 31953 in a preparation is at the optimum state of competence, i.e. the state of optimum uptake of DNA which is necessary for transformation. Five ml volumes of this suspension are put into tubes which in turn are put into a $-70°$ C. freezer and stored until needed. When needed for the method of the invention, the suspension is thawed by placing the tube into a 37° C. $H_2O$ bath.

A freshly prepared suspension of *N. gonorrhoeae* ATCC 31953 can also be used. In this case, the turbidity of the suspension can be anywhere between a quarter of a number 1 McFarland up to a number 4. The suspending medium need not contain the glycerol. The frozen-thawed and the fresh are the preferred preparations of *N. gonorrhoeae* ATCC 31953 for use in accordance with the method of this invention.

A third alternative is to use a suspension made from a lyophilized preparation of *N. gonorrhoeae* ATCC 31953. A suspension at a turbidity of a McFarland 5 or 6 is made in a medium which contains approximately: 1.5% peptone; 0.04% L-glutamic acid; 5% albumin; 5% serum; 5% glycerol; 0.2% starch; 0.4% glucose; 10% sucrose. This medium is adjusted with KOH to a pH of about 7.2. The suspension is then lyophilized.

The lyophilized preparation is reconstituted in GC buffer and used immediately or reconstituted in GC buffer containing the following growth supplements in gms/100 ml: glucose 0.4 g, glutamine 0.01 g, cocarboxylase 0.00002 g, $Fe(NO_3)_3 \cdot 9H_2O$ 0.0005 g. In the latter case, the reconstituted suspension is incubated for 4-6 hours at 30° C. in a $CO_2$ atmosphere before use. The use of the lyophilized test strain after incubation gives better results, i.e., more colonies in a positive test than the direct use of the lyophilized preparation.

While reference is made to growing *N. gonorrhoeae* ATCC 31953 on the surface of a medium containing agar, specifically GC agar this does not exclude growing *N. gonorrhoeae* ATCC 31953 on or in any medium. For example, a liquid culture in a flask or fermenter may be used. Although reference is made to using GC buffer with or without glycerol, this does not exclude using any other medium suitable for maintaining the viability of *N. gonorrhoeae* ATCC 31953, fresh or frozen. Also while reference is made to the special medium in which *N. gonorrhoeae* ATCC 31953 is lyophilized, this does not exclude using any other medium suitable for lyophilizing *N. gonorrhoeae* ATCC 31953. Because *N. gonorrhoeae* ATCC 31953 is resistant to nalidixic acid and streptomycin, these antibiotics can be added to any of the liquid or solid media used in preparing *N. gonorrhoeae* ATCC 31953 for use. For example, Nal at 5 mcg/ml and Str at 1000 mcg/ml were added to a frozen lot of *N. gonorrhoeae* ATCC 31953, in order to rid it of a contaminant when a lot was subsequently used. Now, as a precaution, these antibiotics are routinely added to the GC buffer with or without glycerol used in preparing a suspension of *N. gonorrhoeae* ATCC 31953, and are added to the medium in which *N. gonorrhoeae* ATCC 31953 is lyophilized.

III. The Preparation of a Patient's Specimen Material

The preparation of a DNA extract involves placing a patient's specimen material into a base which lyses the gonococci and then adjusting the pH of the extract with acid to a pH which is not toxic to *Neisseria gonorrhoeae* ATCC 31953. A variation is to make the preparation of the patient's specimen material by first placing it into GC buffer. In either case, the preparation is generally heated. The preferred base and acid are NaOH and HCl.

NaOH and HCl solutions are prepared by diluting commercially available 10 N or 1 N NaOH solutions and 37%–38% or 1 N HCl solution in GC buffer. Diluting the NaOH and HCl in this buffer is an important procedure. The buffering effect allows one to use a little more or less of the recommended volumes of the NaOH and HCl without changing the pH below 6.0 or above 8.0. This range of pH is tolerated by *N. gonorrhoeae* ATCC 31953 in the transformation test to be performed. KOH or even $NH_4OH$ can be used instead of NaOH. It is expected that any base can substitute for NaOH, even a weak organic base. It is expected that any acid can be used to offset the base, even weak organic acids. In each case, the principle is the same, namely, a base is used to lyse gonococci to release DNA, and an acid is used to adjust pH of the extract to a pH which is not toxic to *N. gonorrhoeae* ATCC 31953.

The volumes of GC buffer, NaOH and HCl can vary. Some of the combinations which were found to be useful are as follows: 0.2–0.3 ml 0.1 N NaOH and 0.3–0.4 ml 0.05 N HCl; 0.5 ml 0.1 N NaOH and 0.6–0.8 ml 0.05 N HCl; 0.5 ml GC buffer, 0.1–0.2 ml 0.5 N NaOH and 0.2 ml 0.2–0.4 N HCl; 0.5 ml GC buffer, 0.1 ml 0.4 N NaOH and 0.1–0.2 ml 0.2 N HCl. The principle is to keep the volumes of GC buffer, NaOH and HCl small enough to minimize dilution of the DNA, but large enough for convenient use in a routine laboratory situation and to adjust a preparation of a patient's specimen material to a pH tolerated by *N. gonorrhoeae* ATCC 31953.

As an aide to seeing that the preparation of a patient's specimen material is near a neutral pH, phenol red at a final concentration of 0.005% is used in the base, acid, GC buffer or even all three. This does not exclude using it at any other useable concentrations. Nor does this exclude using other acid-base pH indicators for the purpose just stated.

The preparation of a patient's specimen material is heated to 60° C.–70° C. for 10 min–15 min. Temperatures as high as 75° C. and time periods as long as 30 min. have been used without any apparent effect on the results. Heating inactivates those microorganisms which remain viable in a patient's specimen material.

As a further precaution against contamination by viable microorganisms in a patient's specimen material, an antibiotic tolerated by *N. gonorrhoeae* ATCC 31953 is added to the GC buffer. An antibiotic can be added to the base and acid as well. An antibiotic can similarly be added to any of the media useful in accordance with the method of this invention. Currently, nalidixic acid and streptomycin are being used at final concentrations of 5 mcg/ml and 1000 mcg/ml, respectively. The concentrations of antibiotics stated does not exclude using these antibiotics at higher concentrations tolerated by *N. gonorrhoeae* ATCC 31953.

Ethyl alcohol at a final concentration of about 70% can be added to the pH adjusted preparation of the patient's specimen material whether it has been heated or not. The use of alcohol may be preceded by an addition of about 0.1% albumin to an extract. The albumin acts as an inert carrier for the precipitate which occurs. The suspension is centrifuged at low speed to pellet the precipitate which contains DNA or the precipitate can be collected on filters. The precipitate is dissolved in a small amount of GC buffer, which may contain antibiotics tolerated by *N. gonorrhoeae* ATCC 31953. The amount of GC buffer added is one-tenth to two-tenths the original volume, resulting in a concentrated DNA preparation. After about 10 minutes at room temperature, the concentrated DNA preparation is useable in the transformation step. The use of a concentrated DNA preparation usually yields more colonies in a positive test than the use of a DNA preparation which is not concentrated.

Ethyl alcohol can also be used to concentrate the DNA while it is being extracted by the base. In this case, an alcohol-base solution extracts and precipitates the DNA simultaneously. Again the addition of albumin is optional. The precipitate can be harvested after centrifugation or after collection on a filter. In both cases the suspending medium, GC buffer, should be at a pH of around 6.0 to offset any residual base in order that the final concentrated DNA solution would not be above pH 8.0.

A virtue of using an alcohol procedure is that the alcohol acts as a germicide to inactivate viable organisms. In most situations, this would eliminate the need for heating the preparation of a patient's specimen material.

IV. A Sample Extraction

A sample extraction procedure is now being presented. A cervical swab is put into a test tube which contains 0.5 ml GC buffer. The cervical swab is mixed in the buffer and left in the tube for the remainder of the extraction procedure or, squeezed against the side of the tube and discarded. To the resultant suspension of mucus and cells is added 0.2 ml of 0.3 N NaOH (containing 0.005% phenol red). After a brief time (approximately 30 seconds) 0.2 ml to 0.3 ml of 0.2 N HCl is added to the extract. The test tube is then heated for 10 minutes in a water bath set at 68° C. After cooling to room temperature, the extract is ready for the transformation step of this invention. This example does not exclude using rectal, urethral or other specimens.

V. The Transformation

The transformation step of the test method of this invention is carried out by applying the preparation of a patient's specimen material to *Neisseria gonorrhoeae* ATCC 31953 which grows poorly at about 36° C. on or in a biological medium which can contain antibiotics at concentrations tolerated by the test strain. The preferred method of applying the preparation to *N. gonorrhoeae* ATCC 31953 is by spotting it onto a lawn of *N. gonorrhoeae* ATCC 31953 which is prepared on a common chocolate agar plate. To prepare this lawn preferably two sterile cotton swabs held side by side are dipped into a suspension of *N. gonorrhoeae* ATCC 31953. These swabs are then evenly smeared on the surface of a chocolate agar plate in a manner similar to that done for an antibiotic disk susceptibility test (Lennette, Spaulding, Truant, Manual of Clinical Microbiology, Amer. Soc. Microbiol., p. 423, 1974). One can use a single swab or any number of swabs, or any other implement or method for seeding a chocolate agar plate with a lawn of *N. gonorrhoeae* ATCC 31593. Although a commercial chocolate agar plate (Baltimore Biological Laboratories, Cockeysville, Md.) has been used in many of my studies, this does not exclude any other useable nutrient agar or chocolate agar whether in a petri dish, any type of container or on any surface. This does not exclude a nutrient agar or chocolate agar or any useable growth medium which contains antibiotics at concentrations which are tolerated by *N. gonorrhoeae* ATCC 31953 and on which *N. gonorrhoeae* ATCC 31593 grows poorly at a temperature around 36° C. in a $CO_2$ atmosphere. This does not exclude a medium containing an ingredient which can substitute for $CO_2$ such as $NaHCO_3$.

After the lawn of *N. gonorrhoeae* ATCC 31953 is spotted with the preparation of a patient's specimen material, the chocolate agar plate is incubated at a temperature around 36° C. in a $CO_2$ atmosphere suitable for growth of *N. gonorrhoeae*. After 27-40 hours incubation, a positive test is seen as an area of colony growth where the preparation was spotted. A negative test shows no area of colony growth at the spotted area.

Although it is preferred to use *N. gonorrhoeae* ATCC 31953 in the form of a lawn, it is within the scope of this invention to use *N. gonorrhoeae* ATCC 31953 in any manner in which gonococcal DNA can be used to stimulate detectable growth of *N. gonorrhoeae* ATCC 31953 under conditions which are inhibitory for example, prohibitive temperatures. This means that the test could be run in a liquid environment, with or without antibiotics tolerated by *N. gonnorhoeae* ATCC 31953, containing the *N. gonorrhoeae* ATCC 31953 and gonococcal DNA as long as the presence of that DNA accounts for the growth of *N. gonorrhoeae* ATCC 31953 which would not take place without the gonococcal DNA.

VI. Supporting Data

The efficacy of the test method in accordance with the method of this invention was shown in a blind study done in collaboration with the Centers for Disease Control in which the results of the method of this invention were compared to clinical culture analyses. Cervical and rectal specimens from women and urethral specimens from men were collected at a DeKalb County, Ga., clinic. Two swabs were taken from each anatomic site: one was immediately plated on selective medium and processed at the clinic; the other was mailed to Philadelphia, Pa. where the test in accordance with the method of this invention was carried out. The following positive (+) and negative (−) results were obtained:

| METHOD OF | CULTURE METHOD | | | | | |
|---|---|---|---|---|---|---|
| INVENTION | CERVICAL | | RECTAL | | URETRHAL | |
| | + | − | + | − | + | − |
| + | 69 | 2 | 26 | 4 | 74 | 2 |
| − | 2 | 132 | 1 | 128 | 2 | 66 |

With regard to the cervical specimens, 69 were positive and 132 were negative by both test methods. For the 2 cervicals which were positive by the method of this invention but culture negative, the following information is available: one cervical came from a patient who was located, retested and found to be culture positive and again positive by the method of this invention. This patient was infected with *Neisseria gonorrhoeae* which is apparently vancomycin sensitive because upon retesting that patient, *N. gonorrhoeae* was isolated from chocolate agar and not Thayer-Martin medium which contains vancomycin. Because the test in accordance with the process of this invention is independent of any characteristic of *N. gonorrhoeae* infecting humans, other than ability to grow at about 36° C. on chocolate agar in a $CO_2$ atmosphere, the method of this invention detected this positive the first time as well as the second time. In this regard, the method of this invention could be a very valuable test for the diagnosis of gonorrhea in areas where vancomycin sensitive strains of *N. gonorrhoeae* are common (Windall et al., J. Inf. Dis. 142:755, 1980). The second cervical came from a patient who was a contact to gonorrhea and had a positive rectal culture. This means that the patient had gonorrhea. In this case, the rectal as well as the cervical were positive by the method of this invention.

Based on this information, a reasonable conclusion is that there are no false positive tests in accordance with the method of this invention. The test is as specific for the diagnosis of gonorrhea as is the culture method. The sensitivity of the invention test for cervicals, i.e. the number of positives detected is the same as for the culture method sensitivity of 97.3% (71/73).

With regard to the rectal specimens, 26 were positive and 128 negative by both test methods. Of the 4 rectals which were positive by the method of this invention but culture negative, all of the corresponding cervicals were culture positive as well as positive by the test method of this invention. Therefore these specimens came from patients who had gonorrhea. The four rectals in question were most likely false-negative cultures. Based on this information, the sensitivity of the method of this invention for rectals is 96.8% (30/31) compared to the culture method's sensitivity of 87.1% (27/31).

With regard to the urethral specimens, 74 were positive and 66 were negative by both test methods. Concerning the two urethrals which were positive by the test method of this invention but culture negative, both specimens were strongly positive for gonococci by the gram strain method. Therefore, the specimens came from patients who had gonorrhea. The two urethrals in question were most likely false-negative cultures. Based on this information, the sensitivity of the method of this invention for urethrals is the same as the culture method sensitivity of 97.4% (76/78).

In addition to the above data, 68 patients were tested for cures within 14 days after gonorrhea therapy. The results of both test methods were the same, i.e. the specimens from the patients were negative.

The method of this invention may be suitably performed by the use of a test kit. The kit consists essentially of an aliquot of a test strain of *N. gonorrhoeae* which grows poorly at about 36° C. on or in a biological medium. The kit may also include (1) a solid or liquid medium capable of supporting growth of the test strain, (2) a supply of a base, with or without ethanol, (3) a supply of an acid, (4) a pH indicator and (5) laboratory equipment or supplies. A test strain may be provided as a fresh culture or suspension, as a frozen suspension, as a lyophilized or dry preparation. The preferred biological medium is a chocolate agar or any other nutritional agar in any shape or form on which a test strain barely grows at a temperature around 36° C. in a $CO_2$ atmosphere suitable for *N. gonorrhoeae*.

What is claimed is:

1. A biologically pure culture of the microorganism *Neisseria gonorrhoeae* ATCC 31953 capable of taking up gonococcal DNA, but which microorganism is abnormal in that it has characteristically poor growth on common chocolate agar at a temperature within the range of from about 30° C. to about 37° C. in a $CO_2$ atmosphere suitable for growth of normal *Neisseria gonorrhoeae*, and said microorganism having resistance to naldixic acid and streptomycin at the 5–10 mcg/ml level and the 1000 mcg/ml level or greater, respectively.

2. A biologically pure culture in accordance with claim 1 in the form of a preparation selected from the group consisting of (1) a fresh suspension in a buffer solution or a broth from growth of *Neisseria gonorrhoeae* ATCC 31953 on a solid medium, (2) a suspension in a buffer solution or a broth made from a lyophilized or dried preparation of *Neisseria gonorrhoeae* ATCC 31953, (3) a thawed suspension of *Neisseria gonorrhoeae* ATCC 31953 previously frozen to maintain viability, and (4) a broth culture of *Neisseria gonorrhoeae* ATCC 31953.

3. A biologically pure culture in accordance with claim 2 wherein the preparation contains an antibiotic at a final concentration tolerated by *Neisseria gonorrhoeae* ATCC 31953.

4. The method for the laboratory diagnosis of gonorrhea by detecting DNA of *Neisseria gonorrhoeae* in a patient's specimen material, comprising the steps of (1) applying a non-toxic preparation of a patient's specimen material, directly to a culture of *Neisseria gonorrhoeae* ATCC 31953, which has abnormal growth characteristics, which is in or on a biological medium suitable for growth of normal *Neisseria gonorrhoeae*, and (2) observing for the restoration of normal growth to the abnormal growth strain *Neisseria gonorrhoeae* ATCC 31953, in or on the biological medium of step (1), under conditions normal for growth of *Neisseria gonorrhoeae*.

5. The method of claim 4 whereby the patient's specimen material is prepared by contacting it with a base to lyse *Neisseria gonorrhoeae* in the specimen material and then rendering the material non-toxic by the addition of an acid to adjust the pH to that which is tolerated by *Neisseria gonorrhoeae* ATCC 31953.

6. The method of claim 5 wherein the pH adjustment is done in the presence of a pH indicator.

7. The method of claim 5 wherein the base and acid both contain an antibiotic at a concentration tolerated by the test strain *Neisseria gonorrhoeae* ATCC 31953.

8. The method of claim 5 wherein the base and acid are prepared in a peptone containing buffer.

9. The method of claim 8 wherein the peptone containing buffer contains an antibiotic at a concentration tolerated by the test strain *Neisseria gonorrhoeae* ATCC 31953.

10. The method of claim 8 wherein both the base and acid may be inorganic or organic.

11. The method of claim 10 wherein the base is selected from the group consisting of NaOH, KOH or $NH_4OH$ and the acid is HCl.

12. The method of claim 4 wherein the preparation of a patient's specimen material is heated at a temperature from about 60° C. to about 75° C. for a time period from about ten minutes to about thirty minutes to inactivate any viable organisms.

13. The method of claim 4 wherein according to step (2) the restoration of normal growth to *Neisseria gonorrhoeae* ATCC 31953 is observed by the appearance of distinct visible colonies on a biological medium.

14. The method as in claim 13 wherein the biological medium is common chocolate agar.

15. The method as in claim 4 wherein the preparation of a patient's specimen material contains an antibiotic at a final concentration tolerated by *Neisseria gonorrhoeae* ATCC 31953.

16. A diagnostic test kit useful in the diagnosis of gonorrhea by detecting DNA of *Neisseria gonorrhoeae* in a patient's specimen material, the kit comprising:
    (1) a container with an aliquot of a test strain of *Neisseria gonorrhoeae* ATCC 31953 which microorganism is abnormal in that it has characteristically poor growth on common chocolate agar at a temperature within the range of from about 30° C. to about 37° C. in a $CO_2$ atmosphere suitable for growth of normal *Neisseria gonorrhoeae*,
    (2) a container with a solid or liquid medium capable of supporting growth of the test strain, as well as normal *Neisseria gonorrhoeae*, whereby, said aliquot can be applied to the solid or liquid medium and thereon exposed to a preparation of a patient's specimen material which is non-toxic to said abnormal test strain; the development of a normal growth of *Neisseria gonorrhoeae* colonies indicating the presence of *Neisseria gonorrhoeae* DNA in the patient's specimen material.

* * * * *

UNITED STATES PATENT OFFICE
CERTIFICATE OF CORRECTION

Patent No. 4,446,230                     Dated May 1, 1984

Inventor(s) Leonard J. Zubrzycki

It is certified that error appears in the above-identified patent and that said Letters Patent are hereby corrected as shown below:

Column 3, line 6, the comma after "invention" should be a period.
line 7, after "31953" delete the comma.

Column 7, line 31, "31593" should be "31953".
line 40, "31593" should be "31953".

Column 8, line 40, "142:755" should be "142:775".

Signed and Sealed this

Twenty-third Day of October 1984

[SEAL]

Attest:

Attesting Officer

GERALD J. MOSSINGHOFF

Commissioner of Patents and Trademarks